United States Patent [19]

Greenwald et al.

[11] 4,294,251
[45] Oct. 13, 1981

[54] METHOD OF SUCTION LAVAGE

[76] Inventors: A. Seth Greenwald, 2235 Tudor Dr.; Jack M. Geiger, 2713 Hampshire Rd., both of Cleveland Heights, Ohio 44106; Nathaniel C. Narten, 3732 Northhampton Rd., Cleveland Heights, Ohio 44121; Derek S. Porritt, 3263 Granger Rd., Medina, Ohio 44256; Steven P. Combs, 404 DuPont Way, Dayton, Ohio 45433; John J. Brems, 1591 Grace Ave., Lakewood, Ohio 44107

[21] Appl. No.: 170,596

[22] Filed: Jul. 21, 1980

Related U.S. Application Data

[63] Continuation of Ser. No. 952,195, Oct. 17, 1978, abandoned.

[51] Int. Cl.³ .............................................. A61M 1/00
[52] U.S. Cl. ..................................... 128/276; 128/66; 128/240
[58] Field of Search ................. 128/62 A, 66, 92 C, 128/92 CA, 229, 239, 240, 241, 276; 3/1.9-1.913; 433/81

[56] References Cited

U.S. PATENT DOCUMENTS

| | | | |
|---|---|---|---|
| 559,417 | 5/1896 | Spencer | 128/239 |
| 3,085,573 | 4/1963 | Meyer et al. | 128/229 UX |
| 3,208,145 | 9/1965 | Turner | 128/276 |
| 3,416,532 | 12/1968 | Grossman | 128/276 |
| 3,542,017 | 11/1970 | Adams | 128/66 |
| 3,578,884 | 5/1971 | Jacobson | 128/66 |
| 3,930,505 | 1/1976 | Wallach | 128/276 |
| 4,012,842 | 3/1977 | Vit | 128/66 |

OTHER PUBLICATIONS

Zimmer Catalog-Section D, "The Trapezoidal-28 ® Total Hip Replacement" Amstutz, M.D. Feb., 1973, pp. 11-30, inventors in rea as first 3 inventors.

*Primary Examiner*—Robert W. Michell
*Assistant Examiner*—J. L. Kruter
*Attorney, Agent, or Firm*—Fay & Sharpe

[57] ABSTRACT

The suction lavage system of this invention incorporates a pulsatile water lavage in combination with a suction system to improve the interface between a prosthesis, such as a hip replacement, and the interdigitating network of cancellous bone in which it is secured with acrylic cement. The water lavage effectively evacuates the medullary fat and hematopoietic tissue from the trabecular interstices of cancellous bone.

The suction irrigation system comprises a probe having two configurations which assist in impinging water on cancellous bone for evacuating fat and tissue along with water to improve the interface between the bone and cement. It has been found that weakening of the interface through stress may result in loosening of a prosthesis. The probe consists of a water conduit generally located on the outside of a suction conduit. The suction opening is located below the aperture for the pulsatile jet a distance large enough to insure that the apertures are not immersed in irrigating fluid; the apertures may be displaced to the side or down, or some combination of the two. The water jet pulses at about 2100 pulses per minute. In order to operate to maximum advantage, the pulsatile jet must function in an air environment. This is insured by the fact that the suction outflow is greater than the fluid inflow.

The method of this invention, then, relates to preparing cancellous bone to secure a prosthesis, which is achieved by reaming out of the cancellous bone to fit the prosthesis; suction lavaging the cavity with a probe which includes a pulsatile jet of water to evacuate the water, fat and tissue; and securing the acrylic bone cement to the prepared cancellous surface. In the method of this invention, it is possible to increase the interface shear strength of the lavaged preparation by 162%, which is significant in terms of a control which normally uses saline solution.

3 Claims, 7 Drawing Figures

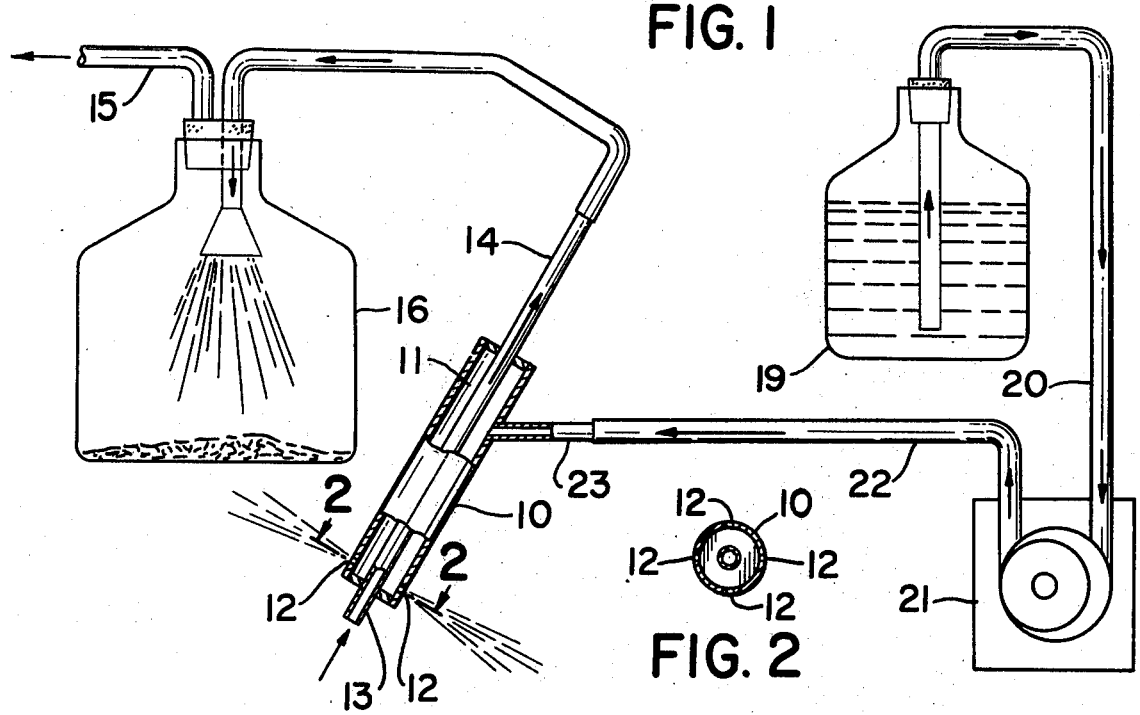
FIG. 1
FIG. 2
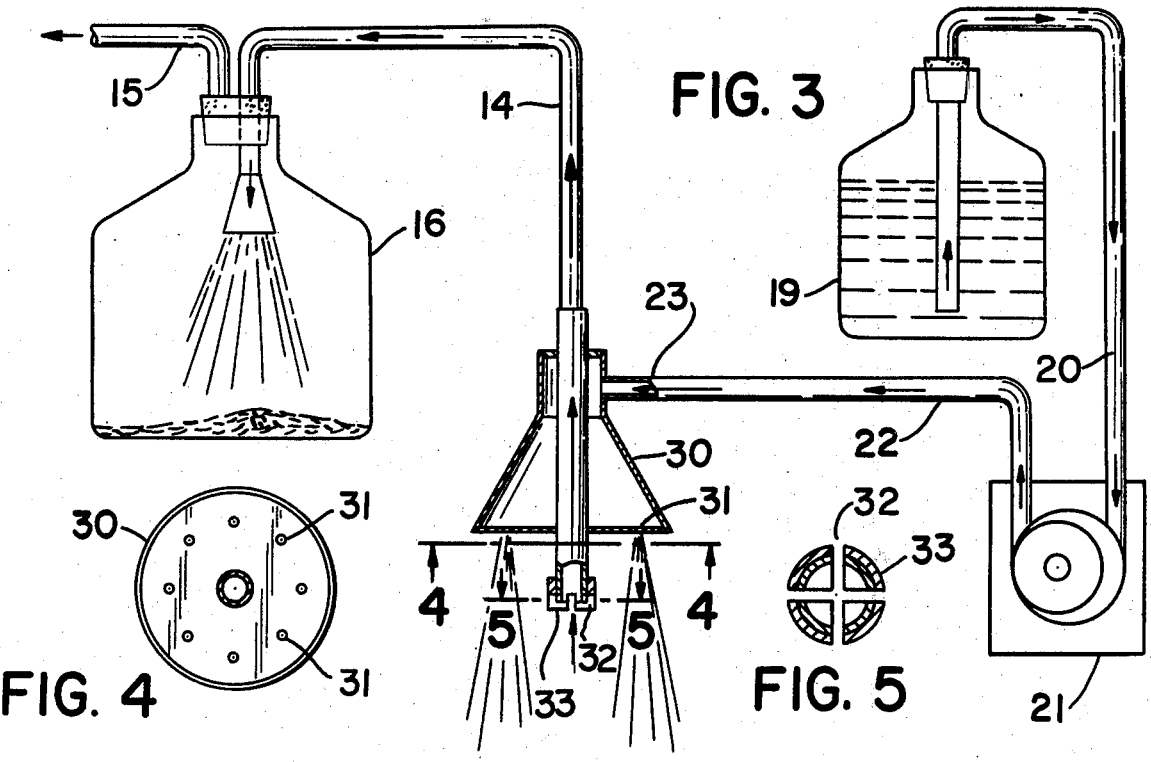
FIG. 3
FIG. 4
FIG. 5
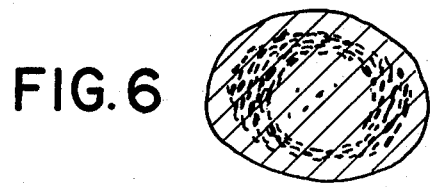
FIG. 6
FIG. 7

METHOD OF SUCTION LAVAGE

This is a continuation of application Ser. No. 952,195, filed Oct. 17, 1978, now abandoned.

BACKGROUND OF THE INVENTION

The bone-cement interface is the key to prosthetic fixation. This bond is a mechanical linkage comprised of an interdigitating network of cancellous bone and cement. Present techniques call for saline treatment of the bone prior to fixation.

Generally in the treatment of wounds, lavage is known as well as suction to remove lavage solutions. In certain ultrasonic surgical practices, such as, for example in Banko U.S. Pat. No. 3,805,787, it has been known to use ultrasonic treatment together with irrigation fluid and/or suction, such as taught in Nehring U.S. Pat. No. 4,112,947, Thompson U.S. Pat. No. 3,012,322, and Wallach U.S. Pat. No. 4,024,866. Further, it has been known to provide pulsed jets of water to a wound as taught in the Stryker lavage systems.

SUMMARY OF THE INVENTION

The present invention relates to a suction irrigation system, which is also referred to as a suction lavage system, to improve the interface between the prosthesis and acrylic cement, and the bone. The object of the system is to clean out the soft tissue prior to inserting the cement to provide better fixation of the prosthetic device.

The suction lavage is performed for at least 30 seconds with a probe having pulsatile water jets outwardly and/or downwardly while suction evacuates the fluids. This prepares the cancellous bone which comprises an interdigitating network by removing and loosening the medullary fat and hematopoietic tissue from the trabecular interstices of the network.

Following lavaging of the bone, acrylic bone cement is injected at a constant pressure. After insertion of the prosthesis and polymerization of the cement, the mechanical linkage between the bone and cement is increased by 162%, and there is a 20% greater penetration of the cement into the trabecular spaces of the bone.

The conclusion is that pulsatile water lavage of cancellous bone surfaces effectively evacuates medullary content to allow for deeper penetration of bone cement into the trabecular interstices, thus yielding a strong mechanical bond.

The probe used in this system is important, in that it allows suction lavaging of deeply reamed cavities in the bone. Another version allows treatment of relatively flat exposed surfaces to remove the medullary content and fluids. The probe has two conduits, one for the pulsed jet of water, and the other for suction, which is longitudinally separated.

BRIEF DESCRIPTION OF THE DRAWING

FIG. 1 is a complete assembly of the suction lavage system, with the probe having one conduit for pulsed water and a second conduit for suction;

FIG. 2 is a cross-section of the probe of FIG. 1;

FIG. 3 is a complete lavage system, with a second version of the probe, having a bell-shaped outer conduit for pulsed water;

FIG. 4 is an end view of the discharge of pulsed water, as shown in FIG. 3;

FIG. 5 is a section through the suction cap of FIG. 3;

FIG. 6 is a horizontal cross-section of the cancellous bone and acrylic cement without suction lavaging; and FIG. 7 is a horizontal cross-section of the cancellous bone and acrylic cement with suction lavaging.

DESCRIPTION OF THE PREFERRED EMBODIMENT

A typical suction lavage system of this invention is shown in connection with FIG. 1, where 10 is a probe having an outer conduit 11 with a plurality of openings for a pulsed water jet as at 12. On the inside is a second conduit at 13 for suction. A tube leads to a source of suction 15 and a flask 16 to trap particulates.

The pulsatile water jet originates from a source of water as at 19, via tubing 20 and a pump 21 which pinches the tubing by means of using an eccentric. The pulsed water jet at about 2100 pulses per minute comes out tubing 22, and is connected to conduit 10 through opening 23. FIG. 2 is a cross-section through opening 12 for the pulsating water jets.

FIG. 3 illustrates a further embodiment, wherein the principal parts of the suction lavage are similarly numbered. Any difference is in the probe where the outer conduit is bell-shaped as at 30 for six or more openings, as shown at 31, which are directed longitudinally towards a working surface from which the water and tissue may be removed through suction cap opening 32. A cross-section through said opening is shown in connection with FIG. 5, where the cap itself is shown at 33. FIG. 4 is an end view of the apertures (31).

The suction lavage system of this invention removes the medullary content of the cancellous bone. The bone itself is lattice-like and interspersed between soft tissue. The object of the lavage is to clean out soft tissue prior to insertion of the cement, and to provide for better fixation of the prosthetic device.

One of the probes is for a hip which is lavaged with four jets of water and, at the same time, evacuates. The probe is most beneficial for the reason that it lavages and provides suction at the same time. In FIG. 1 a probe is shown with four jets at 90 degrees with respect to each other, and at right angles to the end of the probe, as shown in a cavity. Additionally, there is one probe for the knee, as noted in connection with FIG. 3.

FIGS. 6 and 7 illustrate human cadaveric metaphyseal long-bone sections, both before and after suction lavage. In actuality, FIG. 6 shows the normal saline solution treatment, while FIG. 7 is a cross-section after pulsatile water lavage. Pulsatile water lavage of the cancellous bone surface effectively evacuates medullary fat and hematopoietic tissue from the trabecular interstices.

To further emphasize the significance of the present technique, adult human cadaveric metaphyseal long-bone sections are axially drilled through their most cancellous areas. One specimen was placed in normal saline as a control, while the other specimen was exposed to pulsatile water lavage for thirty seconds. Acrylic bone cement was injected at a constant pressure of 60 pounds per square inch into all specimen holes. After polymerization took place, each specimen was placed into an Instron testing machine and subjected to a shearing load at the bone-cement interface until failure. As a result of this demonstration, it was possible to make a comparative evaluation of the interface bond strength for each pair of specimens measured.

In all specimens studied, the interface shear strength of the lavaged preparation specimen was far greater than its control by a factor of 2.62, which also indicates an average increase of 162% in mechanical linkage between bone and cement. Radiographic and visual inspection of the lavaged specimens demonstrated a 20% greater penetration of cement into the trabecular bone, as noted in connection with FIG. 7.

It may be concluded that in the in vitro situation, pulsatile water lavage of cancellous bone surfaces effectively evacuates medullary contents to permit deeper penetration of bone cement into the trabecular interstices, thus yielding a stronger mechanical bond.

The long-term effect of bond enhancement at the bone-cement interface results in a decreased incidence of implant loosening.

The invention has been described with reference to the preferred embodiments. Obviously, modifications and alterations will occur to others upon the reading and understanding of this specification. It is our intention to include all modifications and alterations insofar as they come within the scope of the appended claims or the equivalents thereof.

What is claimed is:

1. A suction lavage method to improve the bond strength of a prosthetic fixation, such as an implant, with reamed cancellous bone, comprising:
   A. applying a pulsatile water jet operating in an air environment to reamed cancellous bone;
   B. applying suction contiguously with the water jet at a greater suction capacity than the water jet flow;
   C. pulsing said water jet at about 2100 pulses per minute;
   D. pressure cementing an implant into the cancellous bone which results in a 20 percent greater penetration of cement into the trabecular interstices of the cancellous bone and greatly improves the bond strength between the implant and the bone.

2. A suction lavage method to improve the bond strength of a prosthetic fixation, such as an implant, with reamed cancellous bone and its trabecular interstices consisting of an interdigitating network having medullary fat and hematopoietic tissue therein, comprising:
   A. applying a pulsatile water jet at about 2100 pulses per minute in an air environment downwardly of the bone;
   B. applying suction to the bone continuously with the suction having a greater capacity than the water jet flow; and
   C. applying bone cement under pressure to cement the implant into the cancellous bone which results in a 20 percent greater penetration of cement into the trabecular interstices of the cancellous bone and greatly improves the bond strength between the implant and the bone.

3. A suction lavage method to improve the bond strength of a prosthetic fixation, such as an implant, with reamed cancellous bone and its trabecular interstices consisting of an interdigitating network having medullary fat and hematopoietic tissue therein, comprising:
   A. applying a pulsatile water jet at about 2100 pulses per minute in an air environment outwardly of the bone;
   B. applying suction to the reamed cancellous bone with the suction having greater capacity than the water jet flow; and
   C. applying bone cement under pressure to cement the implant into the cancellous bone which results in a 20 percent greater penetration of cement into the trabecular interstices of the cancellous bone and greatly improves the bond strength between the implant and the bone.

* * * * *